United States Patent
Pone et al.

(10) Patent No.: US 8,211,045 B2
(45) Date of Patent: *Jul. 3, 2012

(54) ANKLE STRESS RELIEF DEVICE

(75) Inventors: Arnis Pone, Kalamazoo, MI (US); John D. Stahl, Vicksburg, MI (US); Koorosh Naghshineh, Portage, MI (US)

(73) Assignee: Amis Pone, Mattawan, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/462,642

(22) Filed: Aug. 6, 2009

(65) Prior Publication Data

US 2009/0299246 A1    Dec. 3, 2009

Related U.S. Application Data

(63) Continuation of application No. 10/815,376, filed on Apr. 1, 2004, now Pat. No. 7,585,285.

(51) Int. Cl.
*A61F 5/37* (2006.01)
*A61F 13/00* (2006.01)
*A61B 19/00* (2006.01)
*A61F 5/00* (2006.01)
*A61F 13/06* (2006.01)

(52) U.S. Cl. .......... 602/27; 603/5; 603/12; 603/13; 603/23; 603/60; 603/61; 603/65; 128/846; 128/869; 128/882

(58) Field of Classification Search .......... 602/5–6, 602/12–13, 23, 27, 60–61, 65; 128/846, 128/869, 882, DIG. 20
See application file for complete search history.

(56) References Cited

U.S. PATENT DOCUMENTS 5,144,943 A * 9/1992 Luttrell et al. ............. 601/34

OTHER PUBLICATIONS

PCT Application No. PCT/US2005/010828, International Search Report and Written Opinion dated Feb. 5, 2007.
PCT Application No. PCT/US2005/010828, International Preliminary Report on Patentability dated Mar. 8, 2007.
CA Application No. 2,561,507, Office Action dated Oct. 26, 2011.

* cited by examiner

*Primary Examiner* — Patricia Bianco
*Assistant Examiner* — Brandon Jackson
(74) *Attorney, Agent, or Firm* — Henneman & Associates, PLC; Larry E. Henneman, Jr.

(57) ABSTRACT

A novel ankle gapping device includes a lower leg engaging apparatus, a foot engaging apparatus, and a biasing member disposed between the lower leg engaging apparatus and the foot engaging apparatus. The leg engaging apparatus is adapted to securely engage a user's leg such that the leg engaging apparatus will remain stationary when the biasing member exerts an upward force thereon. The foot engaging apparatus is contoured to fit the user's foot. In a particular embodiment, the biasing member is a pneumatic biasing member, such as an inflatable tube that is actuated by a pump. As the pump provides compressed air (or some other fluid) to the biasing member, the pressure inside the biasing member increases, causing an increase in the volume of the biasing member. This pressure and volume increase exerts an upward force via the leg engaging apparatus to the lower leg, and a downward force via the foot engaging apparatus to the foot. The forces applied to the leg and the foot cause separation of the ankle joint, allowing the synovial fluid to flow over the articulating surfaces of the bones of the joint.

19 Claims, 7 Drawing Sheets

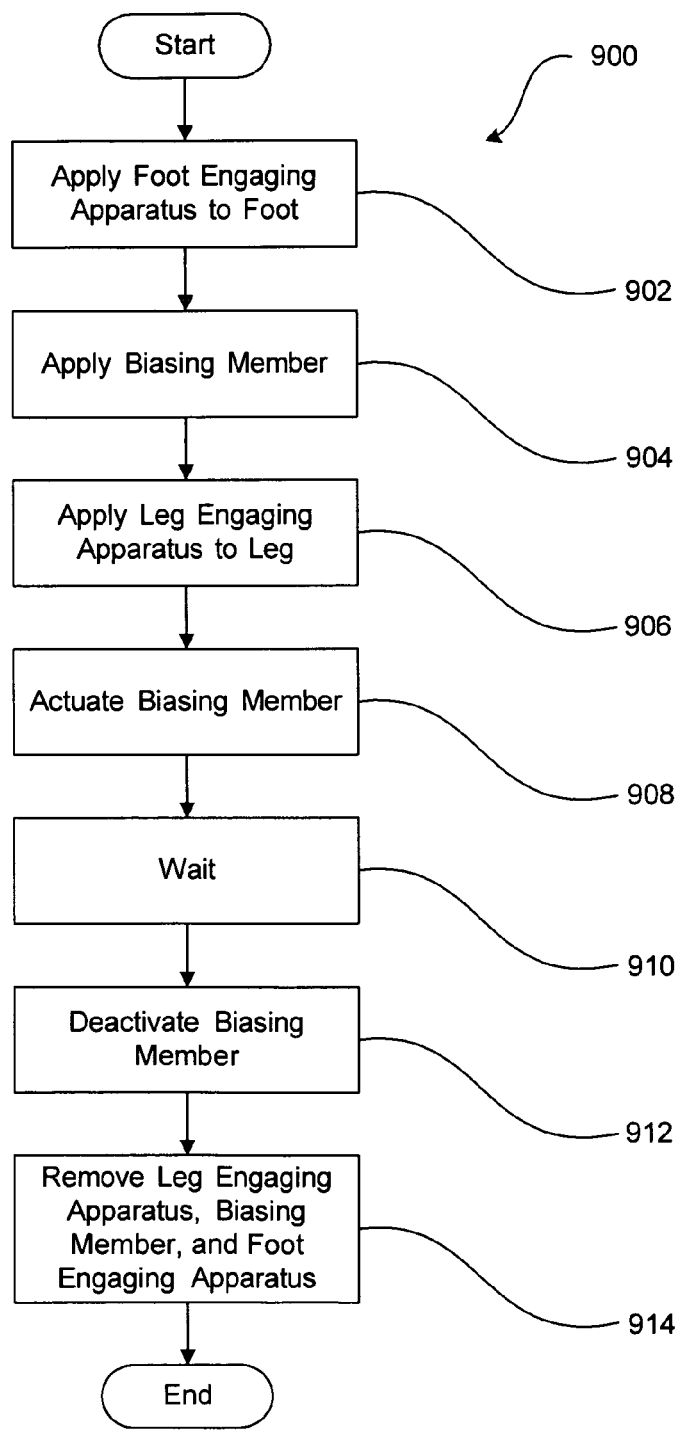

ANKLE STRESS RELIEF DEVICE

RELATED APPLICATIONS

This application is a continuation of U.S. patent application Ser. No. 10/815,376 (now U.S. Pat. No. 7,585,285), filed Apr. 1, 2004 by the same inventors, which is incorporated herein by reference in its entirety.

BACKGROUND OF THE INVENTION

1. Field of the Invention

This invention relates generally to medical devices, and more particularly to a device for relieving ankle pain. Even more particularly, the invention relates to a device for performing a gapping procedure on a human ankle joint.

2. Description of the Background Art

Many people suffer from pain in their ankle joints. The ankle joint is a hinge joint comprising articular surfaces of the distal portion of the tibia and the fibula and the superior surface of the talus. It is wedged shaped, narrow behind and wider in front, with a forty degree range of movement. The line of gravity of the body passes in front of the ankle joint causing restriction and stress to the ankle, which is under constant strain from the effects of gravity.

There are known techniques for relieving pain and stress in the ankle joint, for example by separating or "gapping" the joint to permit the synovial fluid to flow between the articulating surfaces of the bones. In one such technique, the patient lays face down on a table, while the doctor stands on the same side as the ankle being treated. The doctor grasps the patient's heel (e.g., his right heel) with his left hand and places his left elbow in the patient's right popliteal fossa. The doctor then places his right hand over the top of the foot and flexes the foot at a right angle to the leg. The patient's right leg is flexed at the knee by a shift of the doctor's body weight backward, directed through the left arm, until a downward traction separation force is applied to the ankle. Further flexion of the patient's right knee results in a traction force that is transmitted through the left arm, and which gaps the ankle joint.

The ankle gapping procedure described above suffers several disadvantages. Generally the technique is only performed by a doctor or physical therapist and can, therefore, be relatively expensive. It is also inconvenient to make frequent trips to the doctor's office. Additionally, the procedure requires direct participation by the healthcare provider throughout the procedure, and the duration of the treatment is therefore somewhat limited. Furthermore, some care providers are simply not aware of the technique. For any one or more of the foregoing reasons, many people are not able to fully realize the benefits of the ankle gapping procedure.

What is needed, therefore, is a device that permits the patient to undergo an ankle gapping procedure relatively inexpensively. What is also needed is a device whereby a user can perform the ankle gapping procedure without the aid of a doctor or therapist. What is also needed is a device that can be used at any convenient time and place.

SUMMARY

The present invention overcomes the problems associated with the prior art by providing a device for gapping a person's ankle joint sufficient to allow synovial fluid to flow between the articulating surfaces of the bones of the joint. The invention enables a user to perform the ankle gapping procedure at any convenient time or place without the aid or supervision of a health care professional.

One disclosed ankle gapping device includes a leg engaging apparatus, a foot engaging apparatus, and a biasing member disposed there between. When actuated, the biasing member forces the leg engaging apparatus and the foot engaging apparatus away from one another, causing separation of the ankle joint.

In the embodiments shown, the foot engaging apparatus includes a first arched surface to abut the dorsal side of the foot and a second arched surface to abut the heel. In a more particular embodiment, the first arched surface is on a first portion of the foot engaging apparatus, the second arched surface is on a second portion of the foot engaging apparatus, and the first and second portions of the foot engaging apparatus are flexibly coupled together (e.g., by a hinge) to facilitate easy application by a user. A securing device secures the foot engaging apparatus around the foot of the user. The foot engaging apparatus further includes a receiving portion to accept the biasing member. In a more particular embodiment, the receiving portion of the foot engaging apparatus includes a channel formed in a top portion of the foot engaging apparatus.

In another particular embodiment, the leg engaging apparatus is contoured to closely conform a human leg. In a more particular embodiment the leg engaging apparatus is sectioned to facilitate application and removal. A securing device secures the sectioned leg engaging apparatus tightly around the lower leg, such that the leg engaging apparatus remains stationary when a force is exerted thereon by the biasing member. The leg engaging apparatus further includes a receiving portion adapted to accept the biasing member. In a more particular embodiment, the receiving portion of the leg engaging apparatus includes a channel formed in a bottom portion of the leg engaging apparatus.

In one particular embodiment, the biasing member is pneumatic and is actuated by a pump. In the embodiment shown, the pneumatic biasing member is an inflatable tube that is shaped as a sectioned torus, which includes a break to facilitate application and removal.

A method of gapping an ankle using the ankle gapping device is also described. The method includes the steps of applying the foot engaging apparatus to a person's foot, applying the foot engaging apparatus to the person's foot, disposing a biasing member between the foot engaging apparatus and the leg engaging apparatus, and actuating the biasing member. In a particular method, the foot engaging apparatus is applied to the foot by positioning a first portion of the foot engaging apparatus to abut the dorsal portion of the foot and positioning the second portion of the foot engaging apparatus on the heel of the foot. Then, an inflatable tube is positioned in a receiving portion of the foot engaging apparatus. Next, the leg engaging apparatus is applied by wrapping the leg engaging apparatus around the lower leg. Then, the biasing member is actuated by pumping fluid into the inflatable tube.

BRIEF DESCRIPTION OF THE DRAWINGS

The present invention is described with reference to the following drawings, wherein like reference numbers denote substantially similar elements:

FIG. 9 is a flow chart showing one particular method for using an ankle gapping device of the present invention.

DETAILED DESCRIPTION

The present invention overcomes the problems associated with the prior art, by providing a device with which a user can perform an ankle gapping procedure on their own ankle. In the following description, numerous specific details are set forth (e.g., a pneumatic biasing member, particular construction materials, example securing devices, etc.) in order to provide a thorough understanding of the invention. Those skilled in the art will recognize, however, that the invention may be practiced apart from these specific details. In other instances, details of well known medical device manufacturing practices (e.g., molding process, fabrication process, etc.) and components have been omitted, so as not to unnecessarily obscure the present invention.

Figure 1:
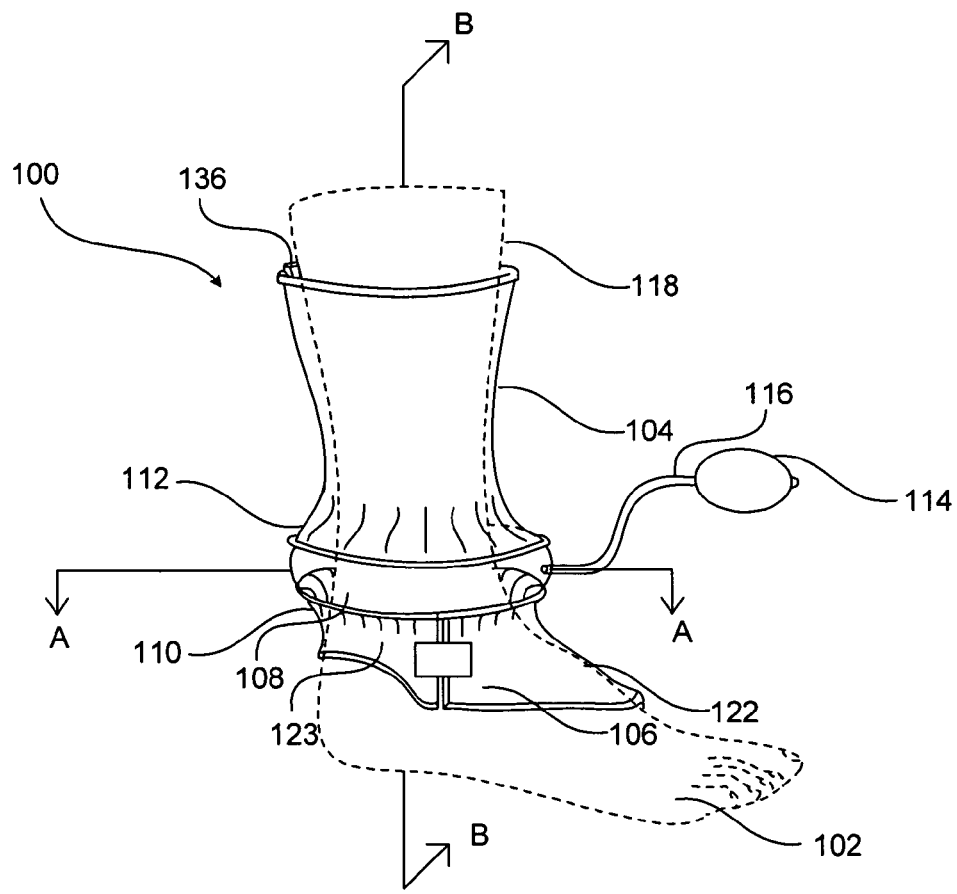
FIG. 1 is a perspective view of an ankle gapping device according to one embodiment of the present invention applied to a human leg.

FIG. 1 shows a perspective view of an ankle gapping device 100 applied to a human foot 102. Ankle gapping device 100 includes a lower leg engaging apparatus 104, a foot engaging apparatus 106, and a pneumatic biasing member 108 disposed between lower leg engaging apparatus 104 and foot engaging apparatus 106. Pneumatic biasing member 108 is shown to be transparent in order to provide a better view of other features of ankle gapping device 100, but it should be understood that biasing member 108 need not be transparent.

Leg engaging apparatus 104 is adapted to securely engage a user's leg 118 such that leg engaging apparatus 104 will remain stationary when pneumatic biasing member 108 exerts an upward force thereon. In this particular embodiment, leg engaging apparatus 104 is made of semi-rigid foam rubber that is wrapped snuggly around user's leg 118. A flared receiving portion 112 of leg engaging apparatus 104 is shaped to accept biasing member 108 and provides a surface against which biasing member 108 can exert force.

Foot engaging apparatus 106 is contoured to fit the user's foot 102. In particular, a front section 122 and a rear section 123 of foot engaging apparatus 106 rest upon the dorsal side and heel of foot 102, respectively. The top rim of foot engaging member 106 defines a flared receiving portion 110 that is shaped to accept biasing member 108 and provides a surface against which biasing member 108 can exert force.

In this particular embodiment, pneumatic biasing member 108 is an inflatable tube and is actuated by a pump 114. Pump 114 is a hand-operated air pump similar to those found in such devices as a sphygmomanometer. As pump 114 provides compressed air (or some other fluid) to biasing member 108, via a supply tube 116, the pressure inside biasing member 108 increases, causing an increase in the volume of biasing member 108. This pressure and volume increase exerts an upward force on receiving portion 112, which is transferred by leg engaging apparatus 104 to lower leg 118, and a downward force on receiving portion 110, which is transferred by foot engaging apparatus 106 to foot 102. The forces applied to leg 118 and foot 102 cause separation of the ankle joint, allowing the synovial fluid to flow over the articulating surfaces of the bones of the joint.

Those skilled in the art will recognize that this particular type of actuator (as well as other described elements, even if not explicitly stated) is not an essential element of the present invention. For example, the present invention may be practiced with alternate actuators, depending on the type of biasing member (e.g., pneumatic, hydraulic, mechanical, magnetic, etc.) used. Such biasing members provide a means for pushing the lower leg engaging means and the foot engaging means in opposite directions. Further, in particular embodiments of the invention, this element may be omitted, for example, by providing an elastic biasing member that is compressed during application of the leg engaging apparatus and/or the foot engaging apparatus.

Figure 2:
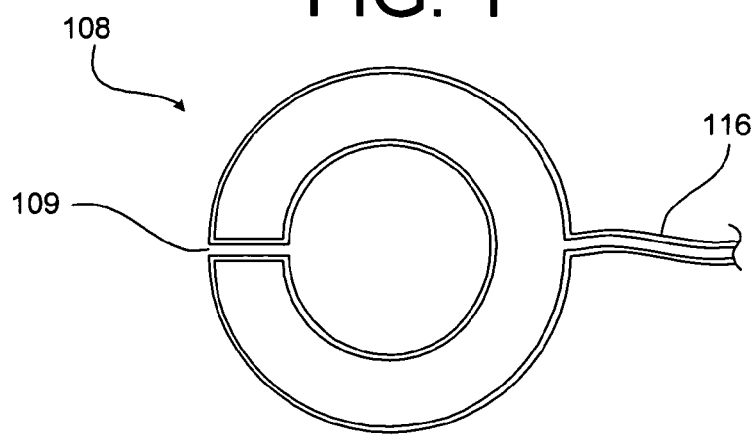
FIG. 2 is a cross-sectional view of a pneumatic biasing member shown in FIG. 1 taken along line A-A.

FIG. 2 shows a top view of pneumatic biasing member 108 to include a sectioned portion 109. Section 109 provides an opening to facilitate the user's application of pneumatic biasing member 108 to his/her ankle, without having to force biasing member 108 over foot 102. Furthermore, section 109 facilitates the application of pneumatic biasing member 108 either before, after, or in between the application of foot engaging apparatus and leg engaging apparatus.

During actuation, pneumatic biasing member 108 increases in volume and takes the shape of a torus. Both receiving portions 112 and 110 at least partially surround pneumatic biasing member 108 (FIG. 1). The torus shape and the uniform internal pressure provides substantially equal expansion all the way around pneumatic biasing member 108, therefore exerting a generally equal force around receiving portions 112 and 110. In particular, the force exerted on the rear sections of receiving portions 112 and 110 is substantially equal to the force exerted on front sections of receiving portions 112 and 110.

It should be noted that pneumatic biasing member 108 need not be a perfectly circular torus. For example, pneumatic biasing member 108 may be slightly elliptical or even rectangular, as long as pneumatic biasing member fits within receiving portions 112 and 110 of leg engaging apparatus 104 and foot engaging apparatus 106, respectively. Therefore, as used herein, the term "torus" is understood to include such deviations from a perfectly circular torus.

Figure 3:
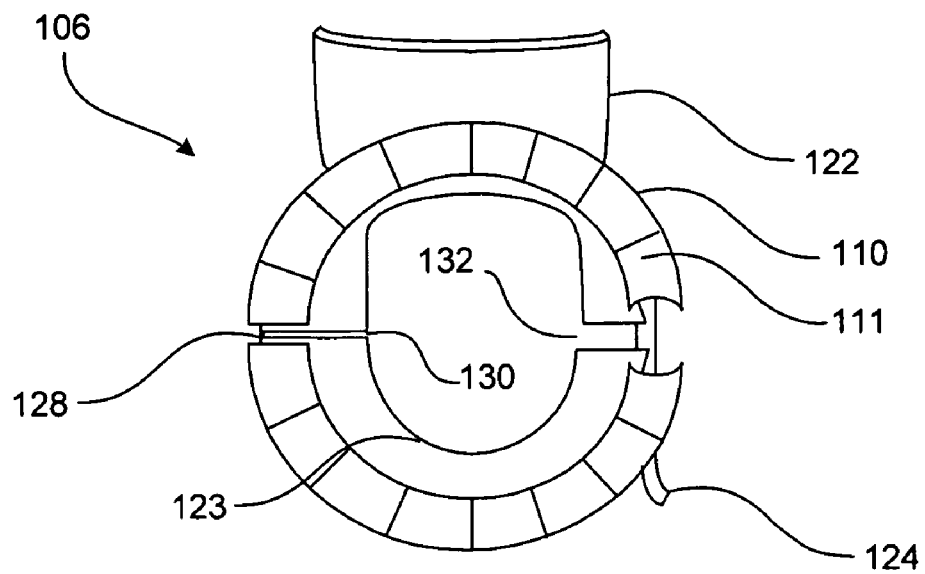
FIG. 3 is a top view of a foot engaging apparatus of the ankle gapping device shown in FIG. 1.

FIG. 3 shows a top view of foot engaging apparatus 106 of ankle gapping device 100 to include a medial separation 130 and a lateral separation 132. Medial separation 130 is bridged by a flexible member to create a hinge-like member 128 that allows foot engaging apparatus 106 to open to receive foot 102. Lateral separation 132 includes a fastening device 124 (e.g., hook and loop material, latch, etc.) to sufficiently secure foot engaging apparatus 106 in a closed and stationary position during actuation of biasing member 108 (FIG. 1).

It should be noted that foot engaging apparatus 106 need not have a separation on each side. Foot engaging apparatus 106 can function with a single separation (e.g., lateral separation 132) as long as foot engaging apparatus 106 is constructed of a semi-rigid, flexible material, for example a flexible plastic material. The material should be flexible enough to open, yet rigid enough to maintain shape during actuation of biasing member 108.

Foot engaging apparatus 106 includes a lower channel 111 formed in receiving portion 110 to seat pneumatic biasing member 108. In particular, lower channel 111 is contoured to the bottom half portion of pneumatic biasing member 108. Furthermore, lower channel 111 is sufficiently rigid to resist deformation under the force of biasing member 108. This helps to maintain equal force on all surface areas of lower channel 111. Separations 130 and 132 continue through lower channel 111 to allow foot engaging apparatus 106 to open.

Figure 4:
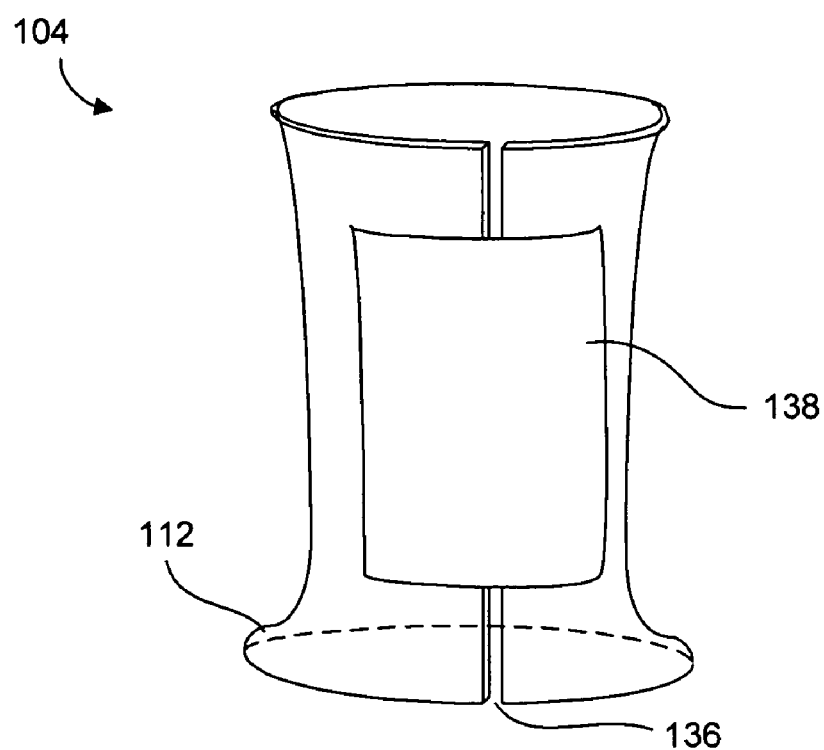
FIG. 4 is a perspective view of a leg engaging apparatus of the ankle gapping device shown in FIG. 1.

FIG. 4 is a perspective view showing leg engaging apparatus 104 to be contoured to fit leg 118. In this particular embodiment, leg engaging apparatus 104 is constructed of a semi-rigid material (e.g., thick foam rubber). This material should be flexible enough for leg engaging device 104 to be wrapped around leg 118, yet rigid enough to maintain its shape when biasing member 108 is actuated. Optionally, the inside of leg engaging apparatus 104 is lined with a resilient material that adheres to the users skin and holds firmly to leg 118.

Leg engaging apparatus 104 includes a receiving portion 112 that provides a seat for the top half of pneumatic biasing member 108. Receiving portion 112 is similar to lower receiving portion 110 in structure and function. In particular, receiving portion 112 transfers an upward force exerted by biasing member 108 to leg engaging apparatus 104, which in turn transfers the force to leg 118.

In this particular embodiment, leg engaging apparatus 104 is sectioned by only one separation 136. Separation 136 enables the user to wrap leg engaging apparatus 104 around leg 118. In the case of a slightly smaller sized leg, leg engaging apparatus 104 can be adjusted by overlapping the ends that meet at separation 136. A fastening member 138 includes an elastic strap with a binding device 140 (e.g., hook and loop fastener material, see FIG. 5) to secure leg engaging apparatus 104 tightly around lower leg 118.

Figure 5:
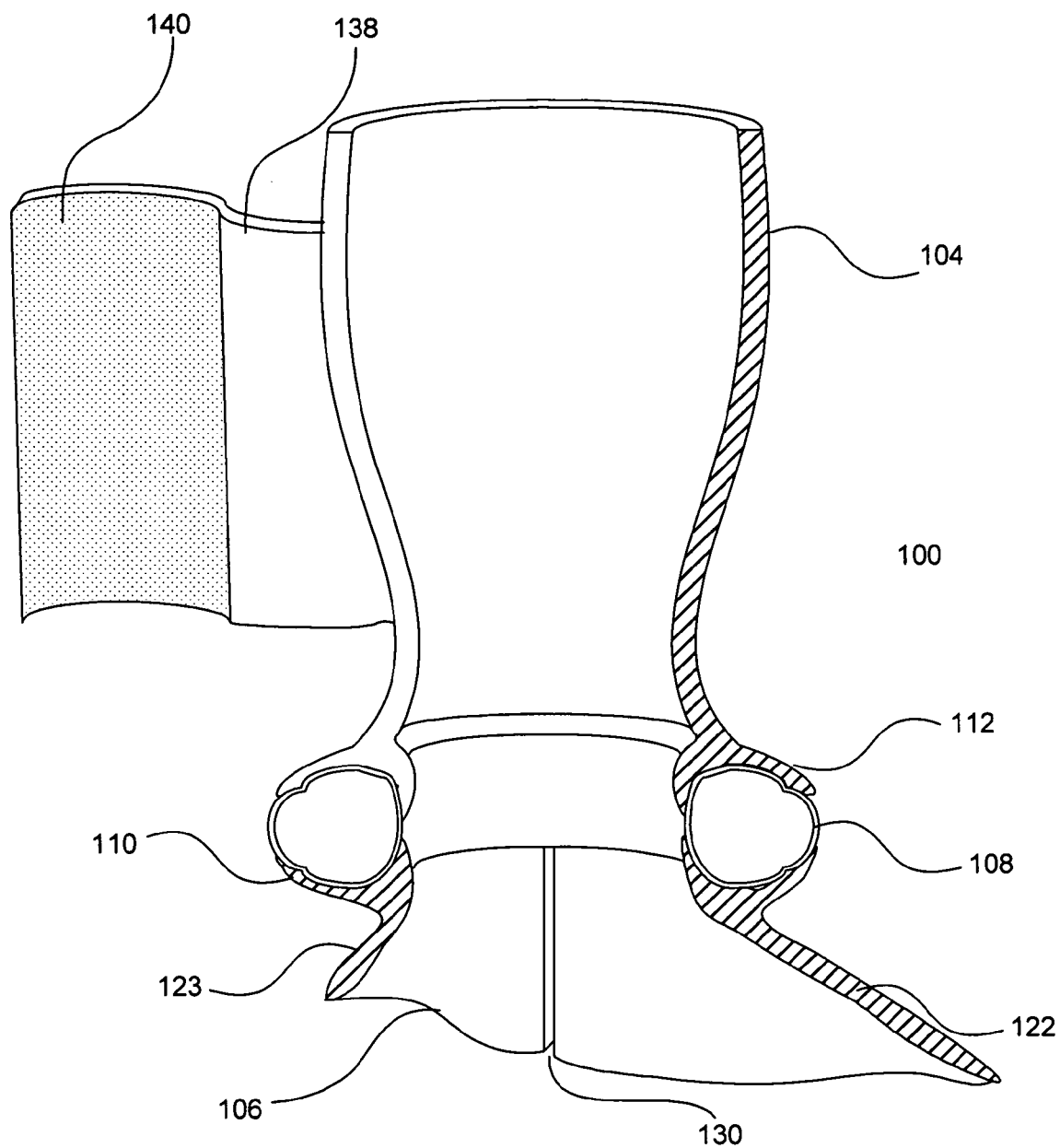
FIG. 5 is a cross-sectional view of the ankle gapping device of FIG. 1 taken along line B-B.

FIG. 5 shows a cross-sectional view of ankle gapping device 100 of FIG. 1 taken along line B-B. Leg engaging apparatus 104 is contoured to leg 118 sufficient to remain stationary with respect to leg 118 during actuation of biasing member 108. In particular, leg engaging apparatus 104 is significantly narrower at the lower end, such that the calf muscle of the user will prevent leg engaging apparatus 104 from riding up leg 118.

Foot engaging apparatus 106 includes a front section 122 and a rear section 123. Front section 122 is shaped to abut the dorsal portion of foot 102. Rear section 123 is shaped to abut the heal of foot 102. In particular, rear section 123 is arched to receive the superior posterior surface of the calcaneus. The interior layer of foot engaging apparatus 106 is resilient to better form to foot 102, to improve adherence to the skin of foot 102, and to be more comfortable.

During actuation of pneumatic biasing member 108, force is exerted evenly upward and downward toward receiving portion 112 and receiving portion 110, respectively. The uniform force applied to receiving portions 110 and 112 maintain receiving portions 110 and 112 in a roughly parallel relationship. Therefore, the angular position of foot 102 with respect to leg 118 depends on the relative position of front section 122 and rear section 123 of foot engaging apparatus 106. In this particular embodiment, foot 102 is maintained at approximately a ninety degree angle with respect to leg 118.

Note that pneumatic biasing member 108 bulges slightly outward between receiving portions 112 and 110 during actuation. So long as the walls of inflatable tube 108 are sufficiently strong, this bulge does not significantly interfere with the function of ankle gapping device 100. If for some reason it is desirable to use an inflatable tube with thinner and/or weaker walls, then the walls of receiving portions 110 and 112 can be extended toward one another to more fully enclose biasing member 108.

Figure 6:
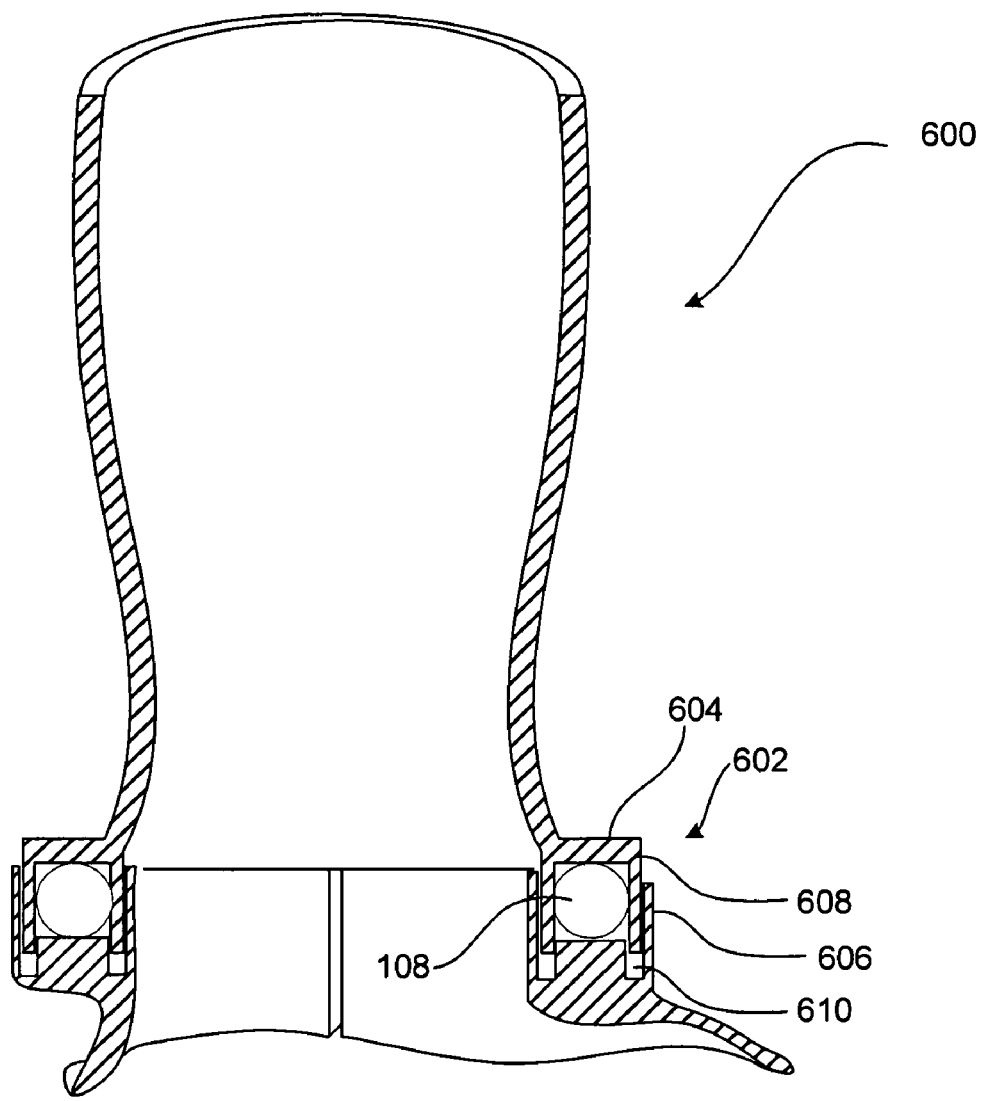
FIG. 6 is a cross-sectional view of an alternate ankle gapping device according to another embodiment of the present invention.

FIG. 6 shows a cross sectional view of an alternate ankle gapping device 600 including an enclosed biasing member receiving portion 602. The enclosed receiving portion 602 includes a rectangular female receiving channel 606 formed to receive a male biasing member housing 604. Male biasing member housing 604 includes lateral walls 608 that slidably engage corresponding grooves 610 formed in female receiving channel 606. This slidable engagement prevents lateral movement while allowing vertical movement.

Because lateral movement is limited and biasing member 108 is completely enclosed by receiving portion 602, force is transferred primarily upward and downward to leg engaging apparatus 104 and foot engaging apparatus 106, respectively. Further, the enclosed receiving portion 602 prevents bulging of biasing member 108, either outward between the ends of the receiving portions or inward against the ankle of the wearer.

Figure 7:
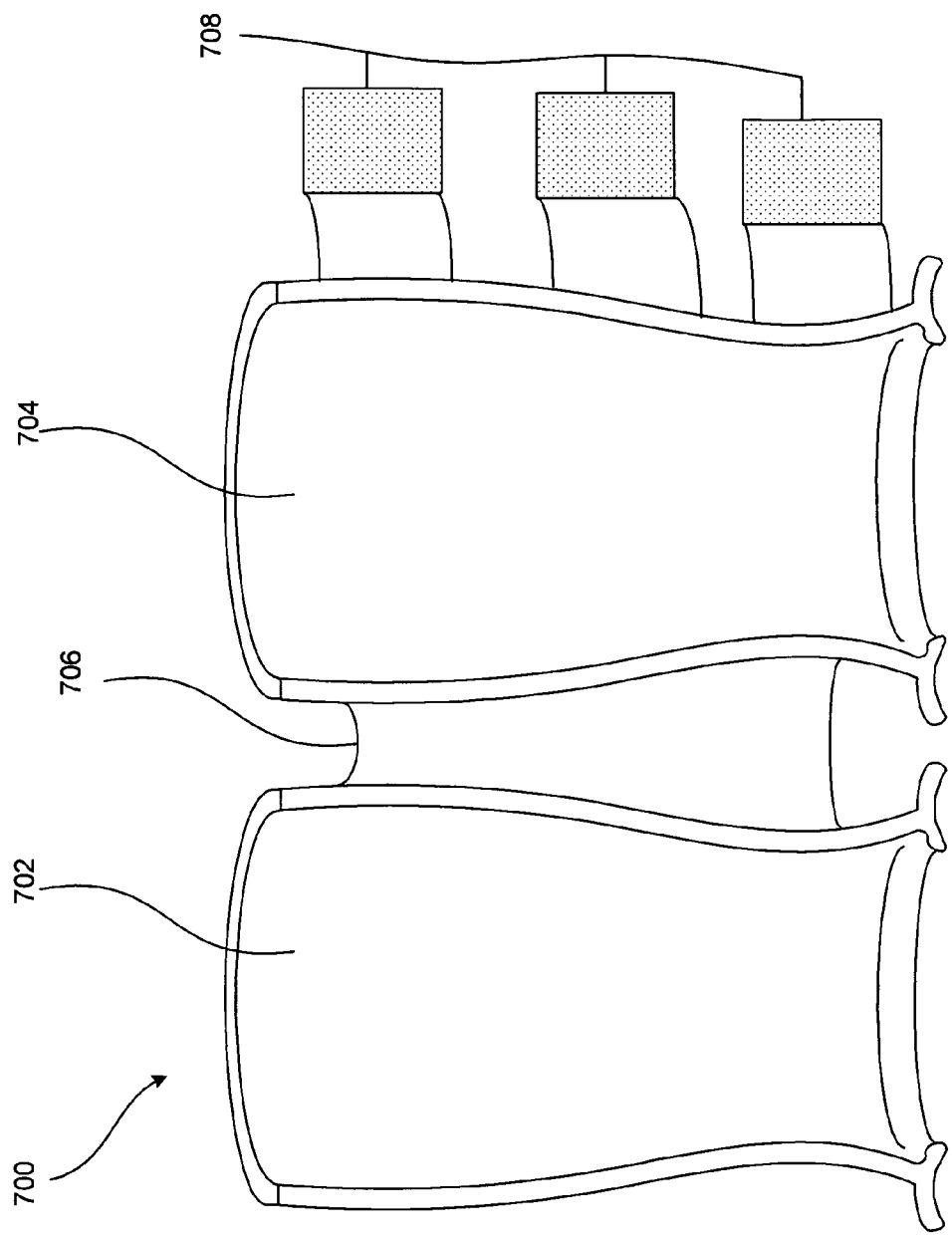
FIG. 7 is an alternate leg engaging apparatus shown in an open position according to another embodiment of the present invention.

FIG. 7 shows a front view of an alternate leg engaging apparatus 700 in an open position. In this particular embodiment, alternate leg engaging apparatus 700 includes a lateral shell 702 and a medial shell 704, connected by a flexible, inelastic hinge 706 (e.g., a sturdy cloth covering). When alternate leg engaging apparatus 700 is applied to a user's leg, lateral shell 702 closely abuts the lateral side of the leg, and medial shell 704 closely abuts the medial side of the leg.

A plurality of fastening members 708 secure alternate leg engaging apparatus 700 to the user's leg. The use of a plurality (three in this example) of fastening members 708 facilitates a tight fit to the leg, because the tightness of fit can be adjusted independently at the location of each of the fastening members 708. In this particular embodiment, fastening members 708 comprise straps of hook and loop fastening material such as that sold under the trade name VELCRO®. However, it is anticipated that other fastening members (buckles, ratchets, latches, etc.) can be used instead.

Figure 8:
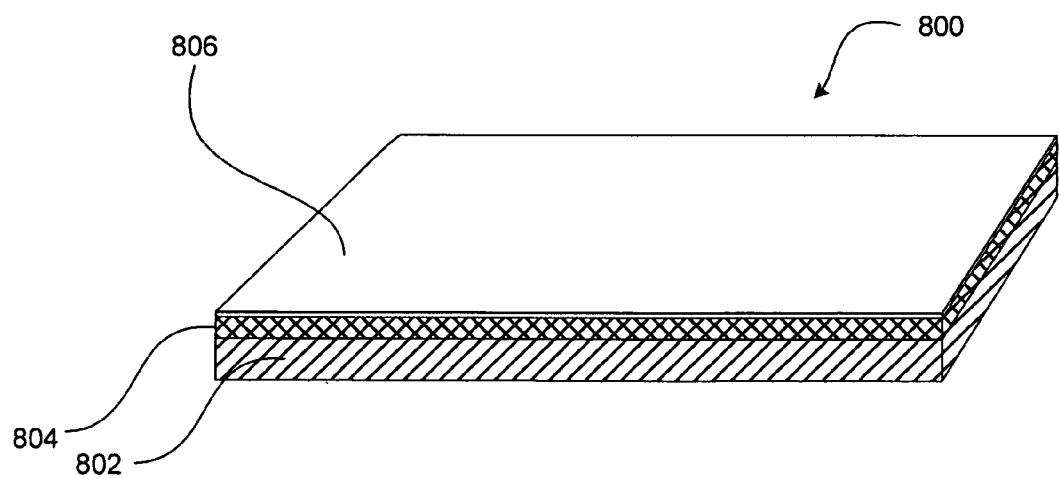
FIG. 8 is a cross-sectional view of a section of construction material of the foot engaging apparatus and the leg engaging apparatus of FIG. 3 and FIG. 7, respectively.

FIG. 8 shows a cross sectional view of a rectangular sample of material 800 from foot engaging device 106 and/or alternate leg engaging device 700. Material 800 includes an inner layer 802, a middle layer 804 and an outer layer 806. The inner layer 802 is made of a resilient, compliant material to conform easily to leg 118 and foot 102. Furthermore, it is desirable for inner layer 804 to be somewhat tacky to help prevent sliding. Middle layer 804 provides structural support for foot engaging apparatus 106 and alternate leg engaging apparatus 700. Middle layer 804 is formed from a sufficiently rigid material (e.g., aluminum, hard plastic, wood, condensed rubber, etc.) to transfer force exerted by biasing member 108 to foot 102 and leg 118 without deforming. Outer layer 806 provides a cover for the exterior of rigid middle layer 802. Outer layer 806 can be function (e.g., include hook and loop fastener material) or merely aesthetic.

FIG. 9 is a flow chart summarizing a method 900 for performing an ankle gapping procedure using ankle gapping device 100 of FIG. 1. In a first step 902, a user applies foot engaging apparatus 106 to his/her foot 102 with rear arched surface 123 abutting the heal and front arched surface 122 abutting the dorsal portion of the foot 102. Then, in a second step 904, the user places biasing member 108 around ankle and into receiving channel 111. Next, in a third step 906, the user applies leg engaging apparatus 104 to his/her lower leg 118. Then, in a fourth step 908, the user actuates biasing member 108 by squeezing pump 114 to inflate biasing member 108. Next, in a fifth step 910, the user waits a length of time corresponding to the recommended duration of the ankle gapping procedure. Then, in a sixth step 912, the user deactivates biasing member 108, for example by deflating it. Finally, in a seventh step 914, the user removes leg engaging apparatus 104, biasing member 108 and foot engaging apparatus 106.

The description of particular embodiments of the present invention is now complete. Many of the described features may be substituted, altered or omitted without departing from the scope of the invention. For example, alternate biasing members (e.g., a mechanical jack type, springs, etc.), may be substituted for the inflatable tube disclosed. As another example, latched bindings, elastic straps and/or buckles may be substituted for the securing devices shown. As yet another example, an alternate leg engaging apparatus can include a top opening of a fixed diameter, which can be slipped over the foot, but that is too small to pass over the calf muscle. These and other deviations from the particular embodiments shown will be apparent to those skilled in the art, particularly in view of the foregoing disclosure.

We claim:

1. An ankle gapping device comprising:
   a lower leg engaging apparatus;
   a foot engaging apparatus; and
   a biasing member disposed between said lower leg engaging apparatus and said foot engaging apparatus to bias said lower leg engaging apparatus and said foot engaging apparatus away from each other; and wherein
   said biasing member is capable of exerting a force sufficient to cause separation of an ankle joint.

2. An ankle gapping device according to claim 1, wherein said foot engaging apparatus comprises:
   a first surface adapted abut a dorsal portion of a foot; and
   a second surface adapted to abut a heel; and
   wherein at least one of said first and second surfaces is arched.

3. An ankle gapping device according to claim 2, wherein:
   said first surface is on a first portion of said foot engaging apparatus;
   said second surface is on a second portion of said foot engaging apparatus; and
   said first portion of said foot engaging apparatus is flexibly coupled to said second portion of said foot engaging apparatus.

4. An ankle gapping device according to claim 1, wherein:
   said foot engaging apparatus defines a seat formed to accept a bottom portion of said biasing member; and
   said leg engaging apparatus defines a seat formed to accept a top portion of said biasing member.

5. An ankle gapping device according to claim 4, wherein said biasing member is an inflatable tube.

6. An ankle gapping device according to claim 1, wherein said biasing member is pneumatic.

7. An ankle gapping device according to claim 1, wherein said foot engaging apparatus includes a receiving portion adapted to accept said biasing member.

8. An ankle gapping device according to claim 1, wherein said leg engaging apparatus includes a receiving portion adapted to accept said biasing member.

9. An ankle gapping device according to claim 1, wherein said leg engaging apparatus is formed of material sufficiently rigid to transfer force exerted by said biasing member to a lower leg of a user.

10. An ankle gapping device according to claim 1, wherein said leg engaging apparatus is sectioned to facilitate application and removal.

11. An ankle gapping device according to claim 1, wherein a relative angle between said foot engaging apparatus and said lower leg engaging apparatus remains constant when said biasing member is biasing said lower leg engaging apparatus and said foot engaging apparatus away from each other.

12. A method for gapping an ankle joint, comprising:
    applying a foot engaging apparatus to a person's foot;
    applying a leg engaging apparatus to the person's leg;
    disposing a biasing member between said foot engaging apparatus and said leg engaging apparatus; and
    actuating said biasing member to move said foot engaging apparatus and said leg engaging apparatus apart from one another, thereby separating the person's ankle joint.

13. A method for gapping an ankle joint according to claim 12, wherein said step of disposing said biasing member between said foot engaging apparatus and said leg engaging apparatus includes positioning an inflatable tube between said foot engaging apparatus and said leg engaging apparatus.

14. A method for gapping an ankle joint according to claim 13, wherein said step of actuating said biasing member includes pumping fluid into said inflatable tube.

15. A method for gapping an ankle joint according to claim 12, wherein said step of applying said foot engaging apparatus to said foot includes positioning a first portion of said foot engaging apparatus on a dorsal side of said foot and positioning a second portion of said foot engaging apparatus on a heel of said foot.

16. A method for gapping an ankle joint according to claim 12, wherein said step of applying said leg engaging apparatus to said leg includes wrapping said leg engaging apparatus around the lower leg.

17. A method for gapping an ankle joint according to claim 12, wherein a relative angle between said foot engaging apparatus and said leg engaging apparatus remains constant after said biasing member is actuated.

18. An ankle gapping device comprising:
    a lower leg engaging apparatus;
    a foot engaging apparatus; and
    means for pushing said lower leg engaging apparatus and said foot engaging apparatus in opposite directions with a force sufficient to gap an ankle joint.

19. An ankle gapping device according to claim 18, wherein a relative angle between said foot engaging apparatus and said lower leg engaging apparatus remains constant as said means for pushing pushes said lower leg engaging apparatus and said foot engaging apparatus in opposite directions.

* * * * *